(12) United States Patent
Ho et al.

(10) Patent No.: US 8,425,473 B2
(45) Date of Patent: *Apr. 23, 2013

(54) SUBRETINAL ACCESS DEVICE

(75) Inventors: Friedrich Ho, Mountain View, CA (US); Stanley R. Conston, San Carlos, CA (US); Ronald K. Yamamoto, San Francisco, CA (US)

(73) Assignee: iScience Interventional Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/359,157

(22) Filed: Jan. 23, 2009

(65) Prior Publication Data

US 2010/0191176 A1 Jul. 29, 2010

(51) Int. Cl.
*A61M 25/00* (2006.01)
*A61M 31/00* (2006.01)
*A61M 1/00* (2006.01)
*A61M 5/32* (2006.01)
*A61M 35/00* (2006.01)

(52) U.S. Cl.
USPC ........... 604/264; 604/521; 604/118; 604/268; 604/272; 604/294

(58) Field of Classification Search ............ 604/22, 604/521, 118, 264, 266, 267, 268, 272, 276, 604/294, 296; 606/107, 108, 109
See application file for complete search history.

(56) References Cited

U.S. PATENT DOCUMENTS

| | | | |
|---|---|---|---|
| 3,659,607 A | 5/1972 | Banko | |
| 4,428,746 A | 1/1984 | Mendez | |
| 4,515,583 A | 5/1985 | Sorich | |
| 4,521,210 A | 6/1985 | Wong | |
| 4,554,918 A | 11/1985 | White | |
| 4,567,882 A | 2/1986 | Heller | |
| 4,607,622 A | 8/1986 | Fritch et al. | |
| 4,735,606 A | 4/1988 | Davison | |
| 4,744,362 A | 5/1988 | Grundler | |
| 4,750,901 A | 6/1988 | Molteno | |
| 4,854,302 A | 8/1989 | Allred, III | |
| 4,862,891 A | 9/1989 | Smith | |

(Continued)

FOREIGN PATENT DOCUMENTS

AU 2004231968 11/2004
CN 286032 Y 7/1998

(Continued)

OTHER PUBLICATIONS

Search Report and Written Opinion dated Mar. 23, 2010 for PCT Patent Application No. PCT/US2010/021865, pp. 1-10.

(Continued)

*Primary Examiner* — Bhisma Mehta
(74) *Attorney, Agent, or Firm* — Weaver Austin Villeneuve & Sampson LLP

(57) ABSTRACT

The invention provides surgical devices that provide access to the sub-retinal space using delicate traction to hold the sensory retina to create and maintain a patent sub-retinal space of sufficient size to introduce and perform treatments on the eye. Such treatments may include the introduction of illumination or imaging agents or tools, surgical tools, the infusion of pharmaceutical or biological agents, and the placement of grafts, transplants or implants and the closure of the site through the delivery of a sealant.

42 Claims, 5 Drawing Sheets

U.S. PATENT DOCUMENTS

| | | | |
|---|---|---|---|
| 4,936,825 A | 6/1990 | Ungerleider |
| 4,968,296 A | 11/1990 | Ritch et al. |
| 5,037,384 A | 8/1991 | Chang |
| 5,059,186 A | 10/1991 | Yamamoto et al. |
| 5,071,408 A | 12/1991 | Ahmed |
| 5,164,188 A | 11/1992 | Wong |
| 5,178,604 A | 1/1993 | Baerveldt et al. |
| 5,180,362 A | 1/1993 | Worst |
| 5,181,922 A | 1/1993 | Blumenkanz et al. |
| 5,273,530 A | 12/1993 | Del Cerro et al. |
| 5,286,261 A | 2/1994 | Roizenblatt |
| 5,300,020 A | 4/1994 | L'Esperance, Jr. |
| 5,338,291 A | 8/1994 | Speckman et al. |
| 5,364,374 A | 11/1994 | Morrison |
| 5,370,607 A | 12/1994 | Memmen |
| 5,370,640 A | 12/1994 | Kolff |
| 5,372,577 A | 12/1994 | Ungerleider |
| 5,397,300 A | 3/1995 | Baerveldt et al. |
| 5,409,457 A | 4/1995 | Del Cerro et al. |
| 5,411,473 A | 5/1995 | Ahmed |
| 5,443,505 A | 8/1995 | Wong et al. |
| 5,486,165 A | 1/1996 | Stegmann |
| 5,487,725 A | 1/1996 | Peyman |
| 5,545,153 A | 8/1996 | Grinblat et al. |
| 5,547,473 A | 8/1996 | Peyman |
| 5,558,629 A | 9/1996 | Baerveldt et al. |
| 5,616,118 A | 4/1997 | Ahmed |
| 5,651,783 A | 7/1997 | Reynard |
| 5,660,851 A | 8/1997 | Domb |
| 5,681,275 A | 10/1997 | Ahmed |
| 5,766,242 A | 6/1998 | Wong |
| 5,785,674 A | 7/1998 | Mateen |
| 5,807,302 A | 9/1998 | Wandel |
| 5,817,075 A | 10/1998 | Giungo |
| 5,824,072 A | 10/1998 | Wong |
| 5,860,923 A | 1/1999 | Lenker et al. |
| 5,882,327 A | 3/1999 | Jacob |
| 5,891,084 A | 4/1999 | Lee |
| 5,893,837 A | 4/1999 | Eagles et al. |
| 5,929,111 A | 7/1999 | Conrow et al. |
| 5,952,378 A | 9/1999 | Stjernschantz et al. |
| 5,962,027 A | 10/1999 | Hughes |
| 5,972,416 A | 10/1999 | Reimels et al. |
| 6,015,403 A | 1/2000 | Jones et al. |
| 6,024,719 A | 2/2000 | Morris |
| 6,036,678 A | 3/2000 | Giungo |
| 6,045,791 A | 4/2000 | Liu |
| 6,050,970 A | 4/2000 | Baerveldt |
| 6,056,700 A | 5/2000 | Burney et al. |
| 6,102,895 A | 8/2000 | Cortella et al. |
| 6,112,747 A * | 9/2000 | Jones et al. .................. 128/830 |
| 6,142,990 A | 11/2000 | Burk |
| 6,149,931 A | 11/2000 | Schwartz et al. |
| 6,156,042 A | 12/2000 | Aramant |
| 6,261,256 B1 | 7/2001 | Ahmed |
| 6,378,526 B1 | 4/2002 | Bowman |
| 6,397,849 B1 | 6/2002 | Bowman et al. |
| 6,402,734 B1 | 6/2002 | Weiss |
| 6,413,245 B1 | 7/2002 | Yaacobi et al. |
| 6,450,984 B1 | 9/2002 | Lynch et al. |
| 6,468,283 B1 | 10/2002 | Richter et al. |
| 6,471,666 B1 | 10/2002 | Odrich |
| 6,508,779 B1 | 1/2003 | Suson |
| 6,524,275 B1 | 2/2003 | Lynch et al. |
| 6,533,768 B1 | 3/2003 | Hill |
| 6,544,249 B1 | 4/2003 | Yu et al. |
| 6,579,256 B2 | 6/2003 | Hughes |
| 6,595,945 B2 | 7/2003 | Brown |
| 6,666,841 B2 | 12/2003 | Gharib et al. |
| 6,668,190 B2 | 12/2003 | Iezzi et al. |
| 6,692,759 B1 | 2/2004 | Wong et al. |
| 6,726,676 B2 | 4/2004 | Stegmann et al. |
| 6,766,817 B2 | 7/2004 | da Silva |
| 6,875,165 B2 | 4/2005 | Dejuan, Jr. et al. |
| 6,908,476 B2 | 6/2005 | Jud et al. |
| 7,122,042 B2 | 10/2006 | LoRusso |
| 7,141,048 B1 | 11/2006 | Charles |
| 7,189,245 B2 | 3/2007 | Kaplan |
| 7,207,980 B2 | 4/2007 | Christian et al. |
| 7,217,263 B2 | 5/2007 | Humayun et al. |
| 7,220,238 B2 | 5/2007 | Lynch et al. |
| 7,247,702 B2 | 7/2007 | Gardner et al. |
| 7,273,445 B2 | 9/2007 | Pulido et al. |
| 7,276,019 B2 | 10/2007 | DeJuan, Jr. et al. |
| 7,285,107 B1 | 10/2007 | Charles |
| 7,285,255 B2 | 10/2007 | Kadlec et al. |
| 7,316,676 B2 | 1/2008 | Peyman et al. |
| 7,331,984 B2 | 2/2008 | Tu et al. |
| 7,699,882 B2 | 4/2010 | Stamper et al. |
| 7,867,186 B2 | 1/2011 | Haffner et al. |
| 8,251,679 B2 | 8/2012 | Kuehner et al. |
| 2001/0011165 A1 | 8/2001 | Engelson et al. |
| 2001/0044595 A1 | 11/2001 | Reydel et al. |
| 2001/0053873 A1 | 12/2001 | Schaaf et al. |
| 2002/0013546 A1 | 1/2002 | Grieshaber et al. |
| 2002/0026176 A1 | 2/2002 | Varner et al. |
| 2002/0026200 A1 | 2/2002 | Savage |
| 2002/0169468 A1 | 11/2002 | Brown |
| 2003/0014036 A1 | 1/2003 | Varner et al. |
| 2003/0236484 A1 | 12/2003 | Lynch et al. |
| 2004/0015140 A1 | 1/2004 | Shields |
| 2004/0039253 A1 | 2/2004 | Peyman et al. |
| 2004/0039401 A1 | 2/2004 | Chow et al. |
| 2004/0050392 A1 | 3/2004 | Tu et al. |
| 2004/0127843 A1 | 7/2004 | Tu et al. |
| 2004/0199130 A1 | 10/2004 | Chornenky et al. |
| 2004/0249404 A1 | 12/2004 | Haefliger |
| 2004/0254520 A1 | 12/2004 | Porteous et al. |
| 2005/0171507 A1 | 8/2005 | Christian et al. |
| 2006/0039993 A1 | 2/2006 | Hughes |
| 2006/0084943 A1 * | 4/2006 | Rosenman et al. ........ 604/890.1 |
| 2006/0110428 A1 | 5/2006 | deJuan et al. |
| 2006/0200097 A1 | 9/2006 | Humayun et al. |
| 2007/0083221 A1 | 4/2007 | Carda |
| 2007/0239066 A1 | 10/2007 | Laham et al. |
| 2007/0244520 A1 | 10/2007 | Ferren et al. |
| 2008/0058704 A1 | 3/2008 | Hee et al. |

FOREIGN PATENT DOCUMENTS

| | | |
|---|---|---|
| DE | 19542955 | 5/1997 |
| EP | 0858788 | 8/1998 |
| EP | 1715827 | 12/2010 |
| JP | 2001-504732 | 4/2001 |
| JP | 2003-524466 | 8/2003 |
| WO | WO93/20784 | 10/1993 |
| WO | WO94/02081 | 2/1994 |
| WO | WO94/02081 A1 | 2/1994 |
| WO | WO94/26175 | 11/1994 |
| WO | WO98/23237 | 6/1998 |
| WO | WO98/30181 | 7/1998 |
| WO | WO 00/64389 | 11/2000 |
| WO | WO 00/64390 | 11/2000 |
| WO | WO01/37767 | 5/2001 |
| WO | WO 01/41685 | 6/2001 |
| WO | WO01/78656 A2 | 10/2001 |
| WO | WO02/32343 A2 | 4/2002 |
| WO | WO02/36052 | 5/2002 |
| WO | WO 02/074052 | 9/2002 |
| WO | WO 02/080811 | 10/2002 |
| WO | WO03/015659 | 2/2003 |
| WO | WO03/045290 | 6/2003 |
| WO | WO2004/026347 | 4/2004 |
| WO | WO2004/093761 | 11/2004 |
| WO | WO2005/107664 | 11/2005 |
| WO | WO2010/085672 | 7/2010 |
| WO | WO2010/085693 | 7/2010 |

OTHER PUBLICATIONS

Office Action dated Sep. 18, 2008 for U.S. Appl. No. 10/528,276, pp. 1-10.

Notice of Allowance dated Dec. 3, 2009 for U.S. Appl. No. 10/528,276, pp. 1-7.

Office Action dated Oct. 15, 2008 for U.S. Appl. No. 11/587,784, pp. 1-18.

Final Office Action dated May 1, 2009 for U.S. Appl. No. 11/587,784, pp. 1-18.

International Search Report dated Apr. 23, 2008 for corresponding European Patent Application No. 03755839.2, pp. 1-5.
Office Action dated Jun. 2, 2009 for corresponding Japanese Application No. 2004-538229, pp. 1-3.
Examination Report dated Apr. 15, 2010 for Canadian Patent Application No. 2,499,094, pp. 1-4.
Examination Report dated Dec. 21, 2009 for European Patent Application No. 03755839.2, pp. 1-4.
Search Report and Written Opinion dated Sep. 1, 2008 for Singapore Patent Application No. 200607413-2, pp. 1-10.
Search Report dated Nov. 5, 2008 for European Patent Application No. 05742275.0, pp. 1-5.
Office Action dated Oct. 31, 2008 for Chinese Patent Application No. 200580021067.2, pp. 1-10.
Written Opinion dated May 28, 2009 for Singapore Patent Application No. 200607413-2, pp. 1-4.
Examination Report dated Mar. 15, 2010 for European Patent Application No. 05 742 275.0, pp. 1-3.
Examination Report dated Feb. 8, 2010 for Indian Patent Application No. 3157/KOLNP/2006, pp. 1-7.
Second Office Action dated Jul. 17, 2009 for Chinese Patent Application No. 200580021067.2, pp. 1-7.
Examination Report dated Apr. 1, 2010 for Australian Patent Application No. 2005240123, pp. 1-4.
Third Office Action dated May 5, 2010 for Chinese Patent Application No. 200580021067.2, pp. 1-10.
Examination Report dated May 6, 2010 for Singapore Patent Application No. 200607413-2, pp. 1-5.
Search Report and Written Opinion dated Apr. 11, 2008 for Singapore Application No. 200607414-0, pp. 1-10.
Examination Report dated Jan. 9, 2009, for Singapore Application No. 200607414-0, pp. 1-5.
Search Report dated Feb. 25, 2009, for European Application No. 05742971.4, pp. 1-5.
Supplementary Search Report dated Apr. 15, 2009, for European Application No. 05742971.4, pp. 1-6.
First Office Action dated Mar. 27, 2009, for Chinese Application No. 200580021068.7, pp. 1-14.
Second Office Action dated Jan. 8, 2010, for Chinese Application No. 200580021068.7, pp. 1-9.
Examination Report dated Jul. 13, 2009, for European Application No. 05742971.4, pp. 1-5.
Examination Report dated Feb. 24, 2010 for Indian Application No. 3158/KOLNP/2006, pp. 1-2.
Examination Report dated Mar. 23, 2010 for Australian Patent Application No. 2005240073, pp. 1-7.
Extended Search Report dated May 11, 2010 for European Patent Application No. 10156474.8, pp. 1-6.
Examination Report dated May 26, 2010 from Mexican Patent Application No. 06/12461, pp. 1-8.
Search Report and Written Opinion dated Mar. 23, 2010 for PCT Patent Application No. PCT/US2010/021842, pp. 1-10.
Jocson, VL, "Air Trabeculotomy", *American Journal of Ophthalmology*, vol. 79, No. 1, pp. 107-111, Jan. 1975.
Krohn J and Bertelsen T, Corrosion Casts of the Suprachoroidal Space and Uveoscleral Drainage Routes in the Human Eye, Acta Ophthalmol Scand. Feb. 1997;75(1):32-5.
Olsen TW, Feng X, et al, "Cannulation of the Suprachoroidal Space: A Novel Drug Delivery Methodology to the Posterior Segment", Am J Ophthalmol. Nov. 2006;142(5):777-87.
Ripart J, Prat-Pradal D, et al, Medial Canthus Episcleral (Sub-Tenon) Anesthesia Imaging, Clin Anat. 1998;11(6):390-5.
Orbis Telemedicine, E-Resources Home, Surgical Management of Strabismus, Chapter 2: Surgical Anatomy, Copyright 2003, pp. 1-3.
Emi et al., "Hydrostatic Pressure of the Suprachoroidal Space", Investigative Ophthalmology & Visual Science, vol. 30, No. 20, Feb. 1989, pp. 233-238.
E-mail dated Jul. 29, 2010 from Elson da Silva re "Respecting Hydrology Science in the Patenting System", regarding US Pat. Application 2010019117, pp. 1-3.
Office Action dated Aug. 19, 2010 for U.S. Appl. No. 12/359,169, (16 pages).
First Office Action dated Aug. 24, 2010 for Japanese Patent Application No. 2007-511094, (3 pages).
Office Action dated Sep. 10, 2010 from Mexican Patent Application No. 06/12460, (3 pages).
Fourth Office Action dated Aug. 20, 2010 for Chinese Patent Application No. 200580021067.2, (10 pages).
Office Action dated Oct. 5, 2010 for Norway Patent Application No. 20065505, (4 pages).
Letter of translation of 2nd Office Action dated Dec. 23, 2010 from Mexican Patent Application No. 06/12460, (2 pages).
Office Action dated Aug. 24, 2010 from Japanese Patent Application No. 2007-511045, (6 pages).
Further Examination Report dated Dec. 3, 2010 for European Patent Application No. 03755839.2, (4 pages).
Second Examination Report dated May 23, 2011 for Australian Patent Application No. 2005240123.
Office Action dated Feb. 18, 2011 for U.S. Appl. No. 12/359,169.
Office Action dated Jan. 6, 2011 for Chinese Patent Application No. 200580021067.2.
Office Action dated Apr. 7, 2011 for Japanese Patent Application No. 2007-511094.
Office Action dated May 27, 2010 for Japanese Patent Application No. 2007-511045.
Office Action dated Sep. 19, 2011 from Korean Patent Application No. 10-2006-7023818.
Office Action dated Sep. 28, 2011 for Korean Patent Application No. 10-2006-7023819.
Notice of Re-examination dated Sep. 23, 2011 for Chinese Application No. 200580048330.7.
U.S. Office Action dated Dec. 28, 2011 issued in U.S. Appl. No. 12/720,543.
U.S. Office Action dated Feb. 2, 2012 issued in U.S. Appl No. 12/720,543.
U.S. Final Office Action dated May 11, 2012 issued in U.S. Appl. No. 12/720,543.
U.S. Office Action dated Mar. 24, 2011 issued in U.S. Appl. No. 11,587,785.
U.S. Final Office Action dated Aug. 26, 2011 issued in U.S. Appl. No. 11,587,785.
U.S. Office Action dated Apr. 17, 2012 issued in U.S. Appl. No. 11,587,785.
U.S. Office Action dated Dec. 8, 2011 issued in U.S. Appl. No. 12/609,345.
U.S. Final Office Action dated Jun. 5, 2012 issued in U.S. Appl. No. 12/609,345.
U.S. Fiunal Office Action dated Aug. 19, 2010 issued in U.S. Appl. No. 12/359,169.
U.S. Office Action dated May 29, 2012 issued in U.S. Appl. No. 12/359,169.
CA Office Action dated Feb. 20, 2012 issued in Application No. 2,564,806.
MX 3rd Office Action dated Mar. 15, 2011 issued in U.S. Application No. 06/12460.
JP Office Action dated Feb. 7, 2012, issued in Application No. 2007-511094.
JP Office Action dated Jul. 3, 2012, issued in Application No. 2007-511094.
EP Search Report dated Jun. 4, 2012 issued in Application No. 12159707.4.
EP Search Report dated May 25, 2012 issued in Application No. 12159708.2.
NO Office Action dated Jul. 14, 2011 issued in Application No. 20065505.
WO International Search Report dated Nov. 10, 2005 issued in Application No. PCT/US2005/015321.
WO International Preliminary Report on Patentability dated Nov. 1, 2006 issued in Application No. PCT/US2005/015321.
WO Written Opinion dated Oct. 29, 2006 issued in Application No. PCT/US2005/015321.
CN Third Office Action dated Oct. 8, 2012 issued in Application No. 200580021068.7.
JP Office Action dated May 31, 2011 issued in Application No. 2007-511045.

Office Action dated Dec. 6, 2011 for Japanese Patent Application No. 2007-511045.
Office Action dated Jul. 26, 2011 for European Patent Application No. 05742971.4.
Search Report dated Sep. 23, 2011 for European Patent Application No. 11174013.0.
WO International Search Report and Written Opinion dated Feb. 10, 2011 issued in Application No. PCT/US2010/053599.
JP Office Action dated Sep. 25, 2012 issued in Application No. 2010-288442.
WO International Preliminary Report on Patentability dated Aug. 4, 2011 issued in Application No. PCT/US2010/021865.
WO International Preliminary Report on Patentability dated Aug. 4, 2011 issued in Application No. Application No. PCT/US2010/021842.
E-mail dated Jul. 29, 2010 from Elson da Silva re "Respecting Hydrology Science in the Patenting System", regarding US Pat. Application 2010019117.
Grover, S., et al., "Normative Data for Macular Thickness by High-Definition Spectral-Domain Optical Coherence Tomography (Spectralis)," *American Journal of Ophthalmology*, 18(2), Aug. 2009, pp. 266-271.
Kim, S., et al., "Comparison of Choroidal Thickness Among Patients With Healthy Eyes, Early Age-Related Maculopathy, Neovascular Age-Related Macular Degeneration, Central Serous Chorioretinopathy, and Polypoidal Choroidal Vasculopathy," *Retina* 31(9), Oct. 2011, pp. 1904-1911.
Norman, R., et al., "Dimensions of the human sclera: thickness measurement and regional changes with axial length," *Exp. Eye Res.* 90(2), Feb. 2010, pp. 277-284.
Tan, C., et al., "Diurnal variation of choroidal thickness in normal, healthy subjects," *Invest. Ophthalmol. Vis. Sci.*, Dec. 13, 2011, 30 pp.
Zhang, X., "In Vivo Cross-Sectional Observation and Thickness Measurement of Bulbar Conjunctiva Using Optical Coherence Tomography," *Investigative Ophthalmology & Visual Science* 52(10), Sep. 2011, pp. 7787-7791.
EP Extended Search Report dated May 25, 2012, issued in Application No. 12150708.2.

\* cited by examiner

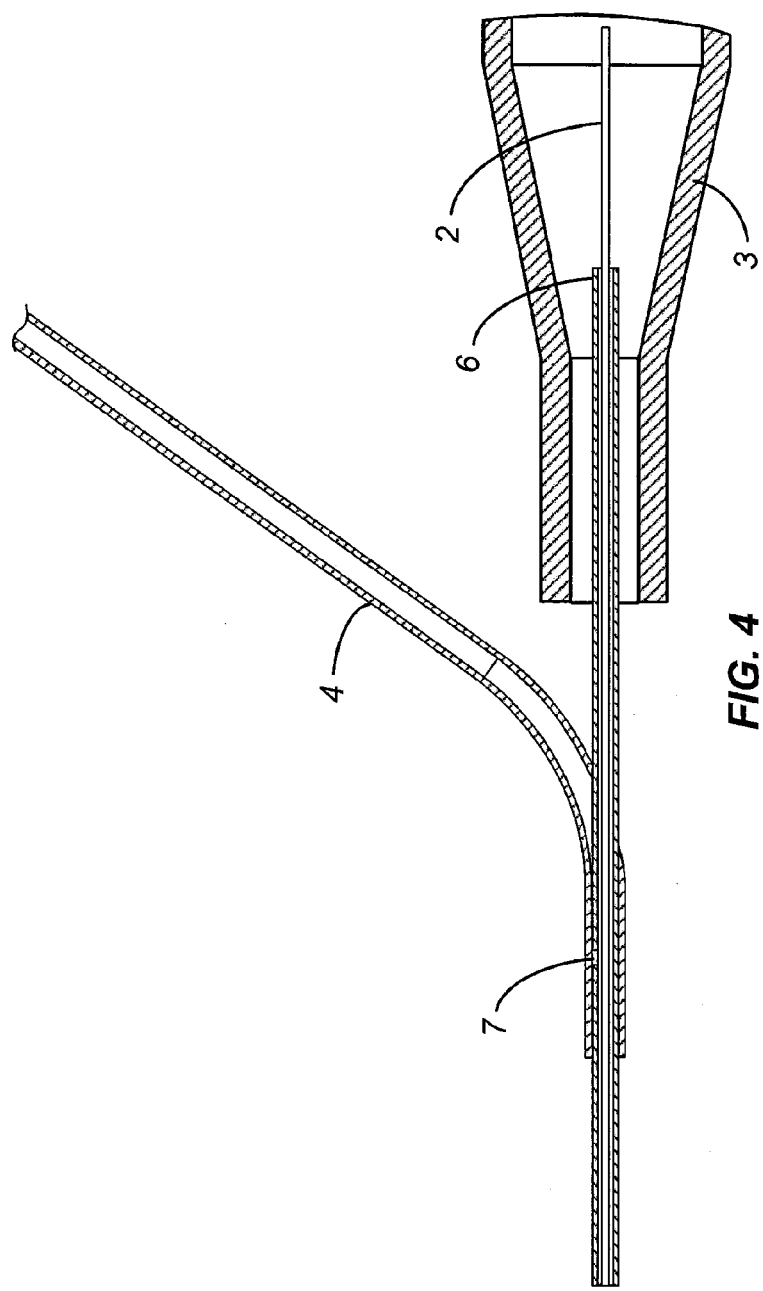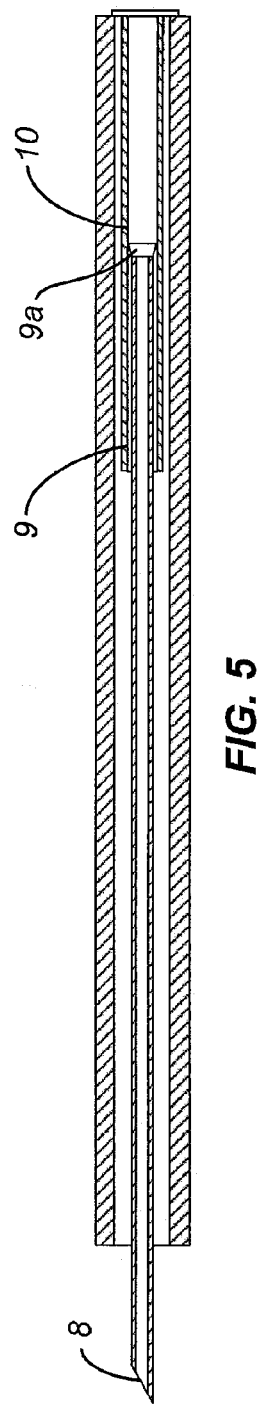
FIG. 4
FIG. 5

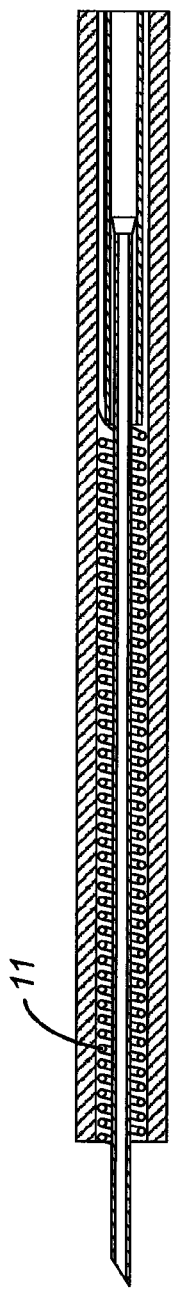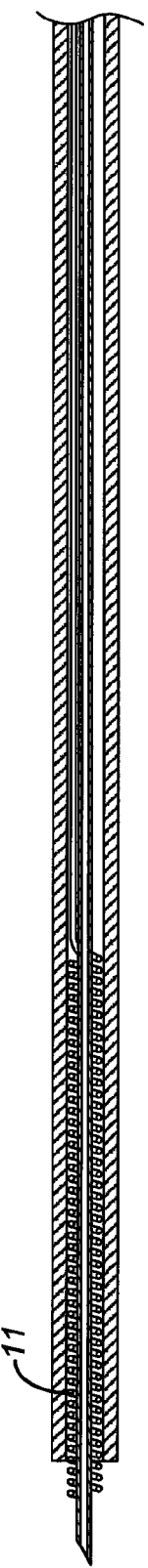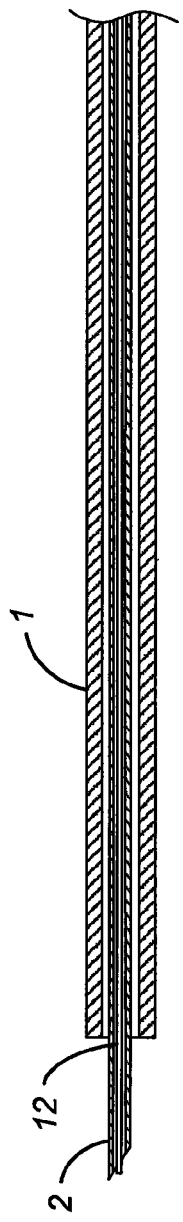

SUBRETINAL ACCESS DEVICE

CROSS-REFERENCE TO RELATED APPLICATION

This application is related to co-pending, commonly assigned Ser. No. 12/359,169, filed on an even date herewith, entitled "Device for Aspirating Fluids" in the names of Chang, Tom S.; Ho, Friedrich; Conston, Stanley R. and Yamamoto, Ronald.

FIELD OF THE INVENTION

The present invention relates to surgical instruments for use in the eye. More particularly, the invention relates to instruments that can provide access to the sub-retinal space using delicate traction to hold the sensory retina to create and maintain a patent sub-retinal space of sufficient size to introduce and perform treatments on the eye. Such treatments may include the introduction of illumination or imaging agents or tools, surgical tools, the infusion of pharmaceutical or biological agents, and the placement of grafts, transplants or implants.

BACKGROUND OF INVENTION

There are many diseases and conditions that affect the posterior segment of the human eye which can lead to a decrease in visual acuity and eventually blindness. Deleterious consequences from disease processes or physio-anatomic defects can affect the tissues of the back of the eye such as the sensory retina, the retinal pigment epithelium (RPE) and the choroid. Diseases such as age-related macular degeneration, diabetic retinopathy, retinopathy of prematurity, choroidal neovascularization, retinitis and macular edema; and conditions such as macular holes, retinal detachments, epiretinal membranes, retinal or choroidal venous occlusions can all lead to vision loss that ranges from mild to total. Many of these ailments are treated through systemic or intravitreal injections of pharmaceutical agents, or via surgery through the vitreous cavity. Procedures such as macular translocation, RPE cellular and tissue transplants or even the placement of retinal implants are new techniques and technologies that require minimally invasive access to posterior tissues in order for the treatments to be applied at site specific locations.

Interventional procedures targeting tissues beneath the sensory retina are difficult to perform due to limited accessibility and the delicate structure of the retina which can be easily damaged during surgical manipulation. It is desired to provide a means of accessing and delivering therapies in a safe manner to the tissues that are not directly accessible via the vitreous cavity. Accessing the sub-retinal space, using delicate traction to hold the sensory retina, would allow for the safe and direct intervention to tissues adjacent to the sub-retinal space including the outer nuclear or photoreceptor layer of the retina and the RPE.

The present invention is directed to surgical devices that can advantageously provide sub-retinal access through an ab-interno approach, by maintaining position on, and protecting the retina while creating and maintaining a patent sub-retinal space of sufficient size to introduce and perform treatment.

SUMMARY

The present invention provides surgical devices for use in the eye, comprising:

a first elongated tubular member having a proximal and a distal end and a lumen passing from the proximal end to the distal end and sized appropriately to pass through a sclerostomy port;

a second elongated tubular member having a proximal end and a distal end, disposed within the lumen of the first tubular member, the second tubular member having a passage therethrough from its proximal end to its distal end;

an annular space within the lumen of the first elongated tubular member, annularly surrounding the second elongated tubular member;

the distal end of the second elongated tubular member having a pointed tip;

the distal end of the first elongated tubular member being open-ended and adapted to be placed in contact with a tissue surface whereby upon reduction of pressure within the annular space, the distal end of the first elongated tubular member seals to the tissue sufficiently such that withdrawal of the first elongated tubular member causes the tissue to detach from other tissues underlying the tissue to form a pocket under the tissue; the pocket accessible to penetration by the pointed tip of the second elongated tubular member through the tissue without damage to the underlying tissues.

In one embodiment, the passage in the first elongated tubular member is in communication with a device for introducing fluids, suspensions, sealants, adhesives, viscous solids or gases, or aspirating fluids, suspensions, viscous solids or gases, through the passage.

In another embodiment, the passage in the second elongated tubular member is in communication with a device for introducing fluids, suspensions, viscous solids or gases, or aspirating fluids, suspensions, viscous solids or gases, through the passage.

In another embodiment the distal end of the second elongated tubular member extends beyond the open distal end of the first elongated tubular member. The second elongated tubular member optimally extends beyond the open distal end of the first elongated tubular member by about 0.005 inch to about 0.125 inch.

In another embodiment the second elongated tubular member is slideably disposed within the first elongated tubular member to treat areas distant from the site of penetration. The second elongated tubular member may also be retractable into the lumen of the first elongated tubular member.

In a further embodiment a blocking member is disposed in the annular space at the distal end of the device, the blocking member having a configuration sufficient to substantially prevent the ingress of tissues into the annular space through the open distal end without preventing fluid flow through the annular space. In some embodiments the blocking member may comprises a coil, a loop or a perforated sheet. The perforations in the sheet may have average diameters in the range from about 0.0001 inch to about 0.005 inch.

In some embodiments the passage in the second tubular member accommodates a surgical instrument or tool. The tool may comprise an imaging instrument, such as an endoscope, or a microsurgical instrument, such as an instrument or tool used for removal of blood clots from tissues or vessels. The instrument comprises a fiber optic instrument, which can be an imaging instrument or adapted to deliver energy at a target site, such as laser energy or radio frequency energy for ablation of tissues or vessels.

In one embodiment the distal end of the device is shaped and dimensioned for access to the sub-retinal space.

In another embodiment the distal end of the device is shaped and dimensioned for access to the tissue of the retinal pigment epithelium.

In a further embodiment the distal end of the device is shaped and dimensioned for access to the tissue of the retina.

BRIEF DESCRIPTION OF THE DRAWINGS

FIG. 4 is a schematic diagram of a device according to the invention at the proximal end.

FIG. 5 is a schematic diagram of a device according to the invention at the distal end.

FIG. 6 is a schematic diagram of a distal tip of a device according to the invention comprising a tissue blocking mechanism flush with distal tip of main shaft.

FIG. 7 is a schematic diagram of a distal tip of device according to the invention comprising a tissue blocking mechanism protruding from distal tip of main shaft.

FIG. 8 is a schematic diagram of a distal tip of device according to the invention comprising a stiffening member disposed within the passage of the second elongated tubular member (a micro needle).

DESCRIPTION OF THE PREFERRED EMBODIMENTS

Figure 1:
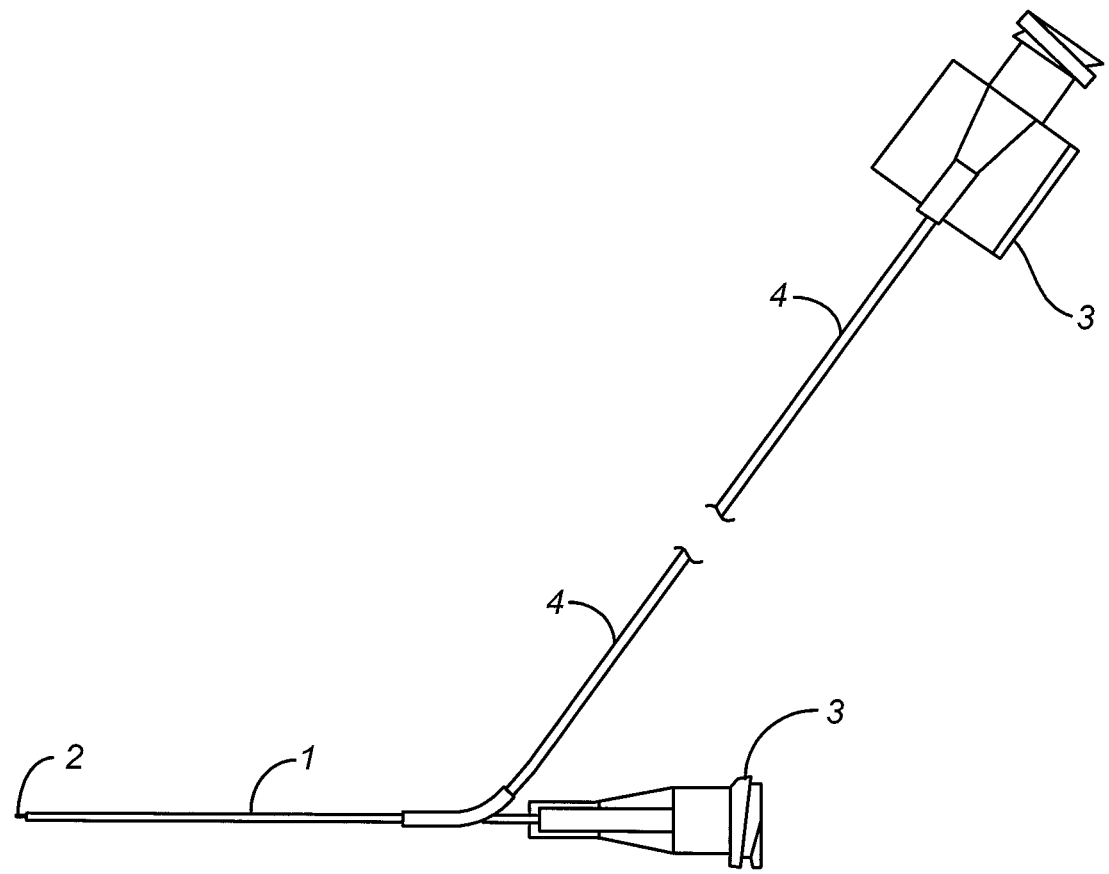
FIG. 1 is a schematic diagram of a subretinal access cannula device according to the invention.

The present invention provides surgical devices to use for access to the sub-retinal space in a human eye in order to introduce therapies to the posterior segment and more specifically to the retina, retinal pigment epithelium and choroid. The devices function advantageously to safely and gently stabilize the sensory retina, while allowing controlled access beneath into the sub-retinal space. The devices advantageously allow for direct tissue access to facilitate surgical, medicinal or biological intervention. The devices are designed to pass through standard sclerostomy ports to access the target site via an ab-interno approach that facilitates direct visualization of the treatment.

The devices of the invention particularly provide access to the sub-retinal space in order to deliver devices, materials, energy, or substances to the adjacent tissues. An advantage of the invention is that use of the devices provides a way to gently hold and maintain position on the retina while therapies are performed beneath the retina.

The devices according to the present invention comprise two elements, a first element designed to use vacuum to hold and stabilize the retina and a second element designed to controllably pierce the retina and provide access to the space beneath.

The first element comprises a first elongated tubular member having a proximal and a distal end and a lumen passing from the proximal end to the distal end. The distal end is open-ended and adapted to be placed in contact with a tissue surface whereby upon reduction of pressure within the first tubular member, its distal end seals to the tissue sufficiently such that withdrawal of the first elongated tubular member or the infusion of fluid into the sub-retinal space causes the tissue to detach from other tissues underlying this tissue to form a pocket under this tissue. The pocket is accessible through penetration by the pointed tip of the second element, by which the second elongated tubular member enters through this tissue without damage to the underlying tissues.

The second element comprises a second elongated tubular member having a proximal end and a distal end, disposed within the lumen of the first tubular member. The second tubular member has a passage from its proximal end to its distal end. The distal end of the second elongated tubular member has a pointed tip.

Each element is in communication to the exterior environment and may optionally be in communication with each other. Various interventional tools and materials may be introduced through the second element, as well as the infusion or aspiration of fluids or gases. A device according to the invention is introduced into the interior of the eye through a sclerostomy port at the pars plana. The device would traverse the vitreous cavity from the pars plana to the target location in the posterior region of the eye.

The first element is primarily designed to use vacuum pressure to hold the retina while preventing ingress of tissues into the element. This functionality serves to stabilize the device location on the retina to allow for interventions to be accomplished beneath the retinal. The first element may also be used for infusion of fluids or gases. In a preferred embodiment, the first element comprises a tubular member which can be attached to an infusion and aspiration source, wherein the aspiration source is used to provide vacuum pressure for stabilization and the infusion source may be used to provide gentle infusion to release the retinal tissues from the first element.

The second element may also comprise a rigid or flexible tubular member, sized appropriately for the specific tool or material being delivered. The second element may be used to house and/or deliver imaging devices or materials to the sub-retinal space. Examples of imaging devices include fiberoptics for endoscopy, optical coherence tomography (OCT), or illumination. The distal tip of the second element may contain mirrors, prisms or lenses to facilitate imaging.

The second element may be used to deliver pharmaceutical or biological agents to the sub-retinal space. Examples of pharmaceutical agents include but are not limited to anti-vascular endothelial growth factors (anti-VEGF), steroids, antibiotics, anti-inflammatories and apoptosis inhibitors. Examples of biological agents include but are not limited to gene therapy agents, radionuclides, stem cell therapy and autologous cell implantation.

The passage in the second element may be in communication with a device for introducing fluids, suspensions, viscous solids or gases through the passage to exit the distal tip. The passage may also be in communication with a device for aspirating fluids, suspensions, viscous solids or gases from the eye through the distal tip.

The passages may terminate at the proximal end in an attachment fitting such as a Luer fitting or quick connecting fitting. The fitting may be attached to a manual syringe, infusion pump, or other device to introduce materials into the passage.

The second element may be used to provide access for surgical therapies. The element may be used to introduce surgical instruments and tools to the space. Examples of surgical tools include but are not limited to forceps, scissors, probes and tissue manipulators. Tools may include imaging instruments such as an endoscope or optic fiber instrument. Tools may comprise, for example, those used for removal of blood clots from tissues or vessels. Other fiber optic instruments may include those adapted to deliver energy to a target, such as laser or RF energy, to ablate tissues or vessels. Examples of therapies that may be aided or enabled by the access device include macular translocation, RPE translocation or transplantation, breakup or dislodging of hemorrhage, dilation or opening of vascular stenoses or occlusions and removal of retinal choroidal anastomoses.

The second element may be used to provide access to the sub-retinal space for the placement of implants such as drug delivery depots, imaging implants, cell implant therapies, such as retinal pigment epithelial tissues, cellular grafts and sensory retina tissues. Furthermore, the second element may be used to provide access for any combination of the aforementioned therapies.

After completion of a treatment as described above, it may be desired to seal the access wound in the retina overlying the sub-retinal treatment. The first element may be used to deliver sealants, adhesives or other means to close the access site upon completion of the therapy. Such sealants or adhesives may include autologous blood, fibrin glue, or biocompatible synthetic polymers that bind or crosslink in-situ.

It is preferred to introduce the device to the posterior chamber with the use of a sclerostomy port. The sclerostomy port is introduced through the sclera at the pars plana to provide access to the posterior chamber. The port provides surface stabilization, sealing to maintain posterior chamber pressure and the ability to interchange surgical tools. Sclerostomy port systems are commercially available to provide access for devices from 20 to 25 gauge in diameter.

Referring to FIG. 1, a device is shown comprising an outer tubular member 1 as the first element, a smaller tubular member 2 following the same axis as the second element, and one or more connection devices 3 for introducing materials into the device or aspirating materials through the device and providing selective communication between the tubular members and other devices. A side arm 4 provides communication with the various pathways created by the geometry of the tubular members.

Figure 2:
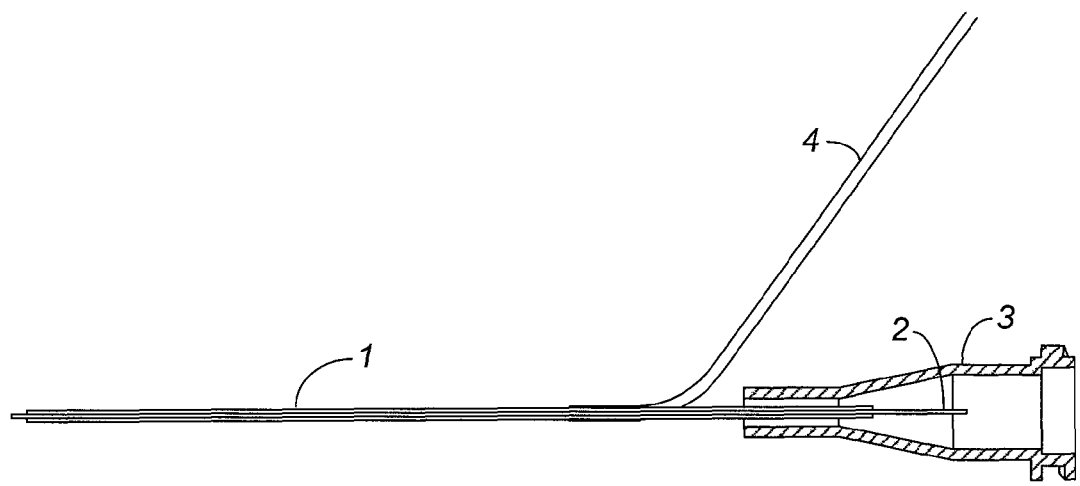
FIG. 2 is a detailed schematic diagram of a subretinal access cannula device according to the invention.

Referring to FIG. 2, the hollow tubular outer member, or main shaft 1, typically has an outer diameter in the range of about 0.010" to about 0.050", for compatibility with conventional sclerostomy ports. The second smaller tubular member, or access shaft 2, is used for access to the sub-retinal space and is placed concentrically within the main shaft. The distal tip of the access shaft may extend beyond the distal tip of the main shaft, typically for a distance in the range of about 0.0015" to about 0.125". Furthermore, the access shaft may be slideably disposed within the main shaft such that the access shaft may be advanced forward and backward as required for treatment of target tissues. The access shaft is disposed coaxially within and along the length of the main shaft, and typically has an outer diameter of about 0.0020" to about 0.010" to minimize injury to the retina when the access shaft pierces the tissue to access the subretinal space. In general, the distal ends of the main shaft and access shaft are of shapes and dimensions suitable for access to the sub-retinal space and the adjacent tissues such as the retina, and/or the retinal pigment epithelium. The access shaft may typically be fabricated of a polymer material, such as polyimide, or a metal, such as stainless steel or nickel-titanium alloy. A side arm 4 provides limited access to the annular space created between the main shaft and the access shaft. When vacuum is applied to the annular space through the side arm, the vacuum present in the annular space will retain the retinal tissues and allow the distal tip of the access shaft to penetrate through the retina. The vacuum level applied to the annular space between the main shaft and access shaft may be determined by the user. When in contact with the retina, the vacuum pressure serves to hold the distal tip of the device in place at one location. The vacuum level may typically be varied from 10-760 mm Hg, and preferably in the range of 10-600 for safe capture of the delicate tissues. The side arm may also be used as a means to infuse fluid through the outer annular space. For example, residual vacuum may keep the sensory retina attached to the outer annular space of the device. A slow, gentle infusion of a safe medium, such as balanced salt solution, may be used to gently release the tissues from the tip of the device. A flowable sealant may also be delivered during device removal to seal the penetration site into the sub-retinal space to prevent leakage of therapeutic substances placed in the sub-retinal site and potential damage to the retina that may be initiated by the penetrating wound. Various instruments or agents may be inserted or removed through the connection device 3 into the subretinal space through the access shaft. The access shaft or the instruments within the access shaft may be advanced in a forward direction to allow treatment of areas distant from the site of penetration. The use of a flexible access shaft facilitates atraumatic advancement within the sub-retinal space. Examples include, but are not limited to, pharmaceutical agents such as steroids or surgical instruments such as probes. The removal of various fluids may also help prevent the build up of subretinal fluid or drug depots.

When the device is connected to a vacuum source and the distal end of the device is placed against the retinal tissue, the outer annular vacuum pulls on and captures the surface of the sensory retina, allowing the access shaft to pierce through the tissue. Alternatively, the access shaft can be pressed against the sensory retina until it pierces through, at which point, vacuum can be applied to retain the retinal tissues away from the distal tip of the access shaft.

Figure 3:
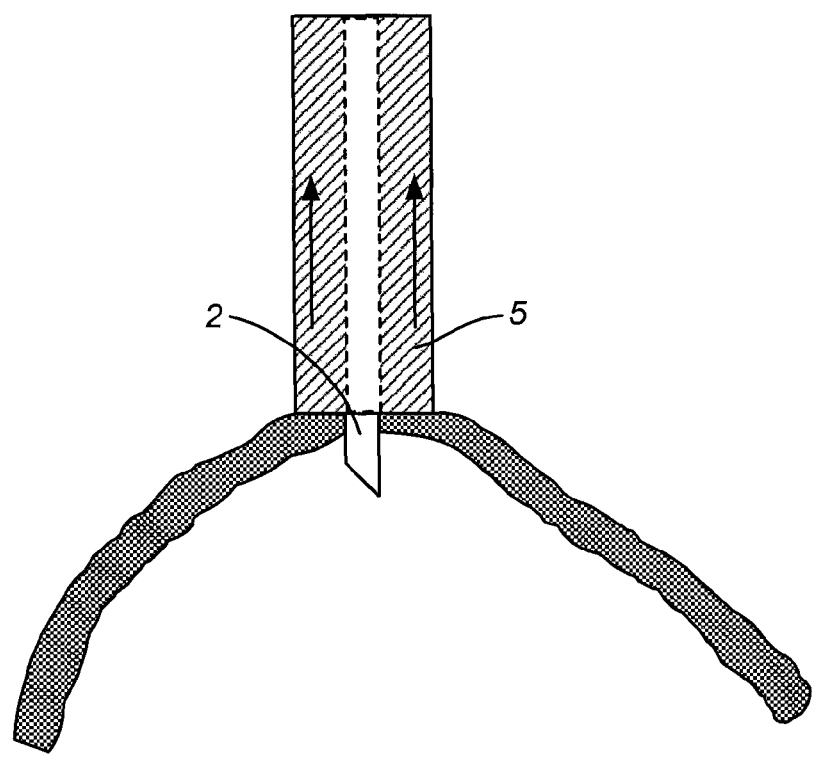
FIG. 3 is a schematic diagram of the operation of the distal tip of a device according to the invention.

Referring to FIG. 3, while the sensory retina is captured and held in place by the outer annular vacuum represented by 5, a protected pocket can be created beneath by gentle injection of balanced salt solution through the access shaft, creating a temporary retinal detachment that can be reversed at the end of the procedure if desired by aspiration of the injected fluid through the access shaft. The distal tip of the access shaft 2 shown residing within this protected space, enables direct access to the sensory layer of the retina, RPE and choroid.

Referring to FIG. 4, the access shaft 2 runs the entire length of the main shaft 6 and beyond the proximal end of the main shaft. The side arm 4 communicates and provides access to the outer annular space of the main shaft through a hole 7 in the main shaft 6 that is in communication with the outer annular space between the main shaft and the access shaft 2. The outer annular space is in communication with one circuit of a connection device (not shown) through the side arm, allowing for manipulation and control of the retina, as well as the potential for the infusion or aspiration of fluids. The access shaft is in communication with another circuit of a connection device 3 allowing for infusion, aspiration, placement of materials or surgical instruments, optical fibers or other therapies.

In another embodiment, as shown in FIG. 5, the access shaft comprises features to facilitate entry into the subretinal space, such as a beveled distal tip 8. To maximize visualization of the access shaft from the proximal end, a larger shaft 10 may overlap with a smaller distal access shaft 9, in which the smaller distal access shaft is utilized to minimize injury to the retinal tissues. The larger shaft 10 may also improve aspiration levels of the access pathway if the access pathway were to be used to aspirate subretinal fluids. An additional feature comprises the gradual flaring 9a of the smaller distal shaft 9 to the larger shaft 10 to create a smooth bore in order to facilitate the introduction of various instruments.

In another embodiment, as shown in FIG. 6, the device further comprises a tissue blocking mechanism 11 to prevent ingress of tissues into the outer annular space between the main shaft and the access shaft. The blocking mechanism may comprise of a coil, wire loop or sheet apparatus with perforations within the outer annular space. Typically the perforations may have average diameters in the range from about 0.0001 inch to about 0.005 inch allowing gases and fluids to pass but excluding tissues. The coil or loop may reside within the distal end of the outer annulus. When vacuum is applied to the device, the coil or loop blocks the entry of tissues into the annular lumen.

In another embodiment, as shown in FIG. 7, the blocking member 11, such as a coil, may extend slightly beyond the distal end of the main shaft 1. When a vacuum is applied to the device, the tissues will apply pressure against the blocking member, causing the member to compress and retract, while simultaneously preventing injury to the tissues and blocking of the access pathway.

In another embodiment, as shown in FIG. 8, the device comprises a stiffening member 12 disposed within the lumen of the access shaft 2 to help prevent kinking. The stiffening member may be a small diameter metallic wire.

Figure 9:
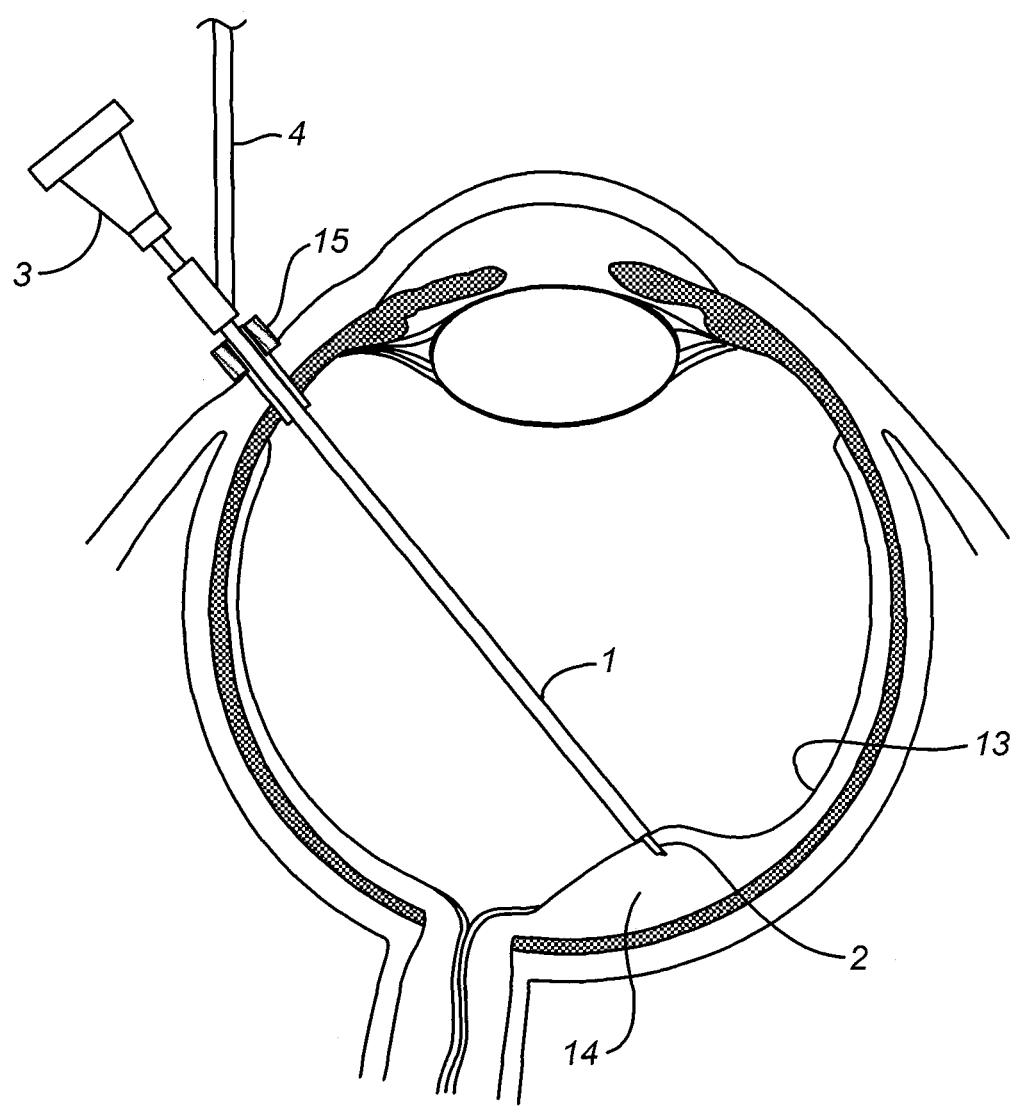
FIG. 9 is a schematic diagram of a device according to the invention deployed through a sclerostomy port and in communication with the subretinal space.

Referring to FIG. 9, a device is shown comprising an outer tubular member 1 as the first element, a smaller tubular member 2 following the same axis as the second element, and one or more connection devices 3 for introducing materials into the device or aspirating materials through the device and providing selective communication between the tubular members and other devices. A side arm 4 provides communication with the various pathways created by the geometry of the tubular members. The device is inserted into the eye through a conventional sclerostomy port 15. While the sensory retina 13 is captured and held in place by the outer annular vacuum, a protected pocket 14 can be created beneath by gentle injection of balanced salt solution through the access shaft, creating a temporary retinal detachment that can be reversed at the end of the procedure if desired by aspiration of the injected fluid through the access shaft. The distal tip of the access shaft 2 shown residing within this protected space, enables direct access to the sensory layer of the retina, RPE and choroid.

The following examples are provided for the purpose of illustration. These examples are not intended to limit the invention.

EXAMPLE 1

Access Device

Approximately 2" of thin walled 25 Gauge stainless steel hypotube, 0.020" by 0.012", (MicroGroup, Inc) was used as the main shaft. A single hole was drilled approximately 1.25" from the distal edge of the hypotube. A skive was created approximately 0.010" from one end of a 3" length of 0.020" by 0.060" Tygon tubing. The main shaft was inserted into the Tygon tubing through the skive until the hole of the main shaft was in communication with the Tygon tubing. UV cure cyanoacrylate adhesive (Loctite 4305, Loctite, Inc.) was applied at the proximal and distal interfaces between the Tygon tubing and the main shaft to create a seal, such that communication existed between the Tygon tubing branching from the main shaft and the lumen of the main shaft.

A 0.028" stainless steel mandrel was heated with the proximal end of the Tygon tubing, and then fed into the proximal end of the Tygon tubing in order to flare the inner diameter of the Tygon tubing from 0.020" to 0.028" for a distance of approximately 0.25". A 6" length of 0.016" by 0.026" Pebax tubing with a luer fitting previously bonded to the proximal end was inserted into the Tygon tubing and bonded at the interface between both pieces of tubing using UV cure cyanoacrylate adhesive.

A polyimide tube with a lumen of 100 microns, an outer diameter of 125 microns, and a length of 0.25" (Microlumen, Inc) was inserted for a distance of 0.05" into another polyimide tube with a lumen of 165 microns, an outer diameter of 210 microns, and a length of 1.85" to form the access shaft. Epoxy (Loctite M-31CL, Loctite, Inc) was applied to bond the two polyimide tubes together.

A stainless steel coil with a length of 0.170", an additional 2.0" length of wire extending beyond the coil, and an outer diameter of 250 microns (Heraeus Vadnais, St. Paul, Minn.) was used as the tissue ingression prevention mechanism. The stainless steel coil was placed over polyimide tube assembly, such that the additional stainless steel wire extended towards the proximal portion. The polyimide tube assembly with the overlaid coil was then inserted into the main shaft and bonded at the interface between the polyimide tubing, stainless steel wire, and main shaft with a UV cure cyanoacrylate adhesive at the proximal end to form a seal. The distal tip of the polyimide tube assembly protruded from the main shaft, and the coil was captured within the main shaft such that the distal end of the coil was flush with the distal end of the main shaft.

The proximal end of the main shaft was inserted into a luer fitting and fixed in position using epoxy. The device provided separate access to the inner polyimide tubing and to the outer annular space created by the polyimide tubing and the main shaft. The Tygon tubing provided access strictly to the outer annular space, while the luer fitting provided access solely to the inner polyimide tubing.

EXAMPLE 2

Laboratory Testing with the Access Device

A human cadaver eye was obtained from an eye bank. The cornea, the iris, natural lens, and the vitreous were removed, providing access to the retina from the interior of the globe without significantly damaging the retina tissue. The open globe was filled with phosphate buffered saline.

An access device as described in Example 1 was set-up as follows. The side port of the device was connected to a vacuum source to provide aspiration in the outer annulus. The vacuum source was capable of providing vacuum levels from 300 to 600 mm Hg. A 6 inch long extension tube was attached to Luer fitting in communication with the access shaft distal tip. A syringe containing 0.1% Alcian Blue dye was attached to the extension line.

In a first trial, the device tip was placed against a portion of the cadaver eye retina that had detached from the underlying RPE during preparation. Vacuum aspiration was applied to the outer annulus and its attachment to the retinal surface was confirmed by applying slight traction on the tissues with the device. With the outer annulus in place on the retinal surface, the inner access shaft entered the sub-retinal space. Alcian Blue was injected into the sub-retinal space and was seen to flow under the retinal tissues. The injection was stopped, the vacuum was released and the device removed from the eye. The dye was visually confirmed to be under the retina and not in the vitreous cavity.

In a second trial, the device was placed against a portion of the cadaver eye retina which was still attached to the underlying tissues. The device was pushed down until the outer annulus contacted the retinal surface at which time the vacuum aspiration of the outer annulus was applied. Attachment of the device to the retina was confirmed by applying traction to lift the tissues. The retina was lifted upwards, creating a working pocket underneath. Alcian Blue dye was injected into the pocket and was seen to spread in the cavity under the retinal tissues. After completing the injection, vacuum aspiration was applied to the micro-needle and fluid/dye was removed from the sub-retinal pocket.

What is claimed is:

1. An apparatus for use with an eye comprising:
   a first elongated tubular member having a proximal and a distal end and a lumen passing from said proximal end to said distal end wherein said distal end is shaped and dimensioned for access to the tissue of the retina;
   a second elongated tubular member having a proximal end and a distal end, disposed within said lumen of said first tubular member, said second tubular member having a passage therethrough from said proximal end to said distal end;
   an annular space within the lumen of said first elongated tubular member, annularly surrounding said second elongated tubular member; and
   a blocking member disposed within said annular space, said blocking member having a configuration to allow passage of gases and fluids, and to block entry of tissues into said first elongated tubular member through said annular space with a blocking member distal end that extends beyond said annular space at the distal end of said first elongated tubular member to prevent injury to tissue within the eye by being caused to compress and retract into the distal end of said first elongated tubular member upon reduction of pressure within said annular space;
   the distal end of said second elongated tubular member having a pointed tip;
   said distal end of said first elongated tubular member being open-ended and adapted to seal upon placement from within the eye in contact of said distal end of said first elongated tubular member with the surface of a tissue layer and upon reduction of pressure within said annular space to allow said pointed tip of said second elongated tubular member to pierce said tissue layer, whereby upon withdrawal of said first elongated tubular member sealed to said tissue layer, said tissue layer detaches from other tissues underlying said tissue layer to form a pocket under said tissue layer accessible to penetration into said pocket by the pointed tip of said second elongated tubular member through said tissue layer without damage to said underlying other tissues.

2. An apparatus for use with an eye comprising:
   a first elongated tubular member having a proximal and a distal end and a lumen passing from said proximal end to said distal end wherein said distal end is shaped and dimensioned for access to the tissue of the retina;
   a second elongated tubular member having a proximal end and a distal end, disposed within said lumen of said first tubular member, said second tubular member having a passage therethrough from said proximal end to said distal end;
   an annular space within the lumen of said first elongated tubular member, annularly surrounding said second elongated tubular member; and
   a blocking member disposed within said annular space, said blocking member having a configuration to allow passage of gases and fluids, and to block entry of tissues into said first elongated tubular member through said annular space upon reduction of pressure within said annular space with a blocking member distal end that is disposed flush to the distal end of said first elongated tubular member;
   the distal end of said second elongated tubular member having a pointed tip;
   said distal end of said first elongated tubular member being open-ended and adapted to seal upon placement from within the eye in contact of said distal end of said first elongated tubular member with the surface of a tissue layer and upon reduction of pressure within said annular space to allow said pointed tip of said second elongated tubular member to pierce said tissue layer, whereby upon withdrawal of said first elongated tubular member sealed to said tissue layer, said tissue layer detaches from other tissues underlying said tissue layer to form a pocket under said tissue layer accessible to penetration into said pocket by the pointed tip of said second elongated tubular member through said tissue layer without damage to said underlying other tissues.

3. The apparatus according to claim 1 or 2 wherein said passage in said second elongated tubular member is in communication with a device for introducing fluids, suspensions, sealants, adhesives, viscous solids or gases, or aspirating fluids, suspensions, viscous solids or gases, through said passage.

4. The apparatus according to claim 3 wherein said second elongated tubular member comprises a polymer.

5. The apparatus according to claim 4 wherein said polymer comprises a polyimide.

6. The apparatus according to claim 3 wherein said device in communication with said passage is capable of delivering a sealant in the form of autologous blood.

7. The apparatus according to claim 3 wherein said device in communication with said passage is capable of delivering a sealant in the form of fibrin glue.

8. The apparatus according to claim 3 wherein said device in communication with said passage is capable of delivering a biocompatible synthetic adhesive.

9. The apparatus according to claim 3 wherein said device in communication with said passage is capable of delivering liquids through said passage.

10. The apparatus according to claim 3 wherein said device in communication with said passage is capable of delivering tissues through said passage.

11. The apparatus according to claim 10 wherein said tissues comprise cellular grafts.

12. The apparatus according to claim 10 wherein said tissues comprise retinal pigment epithelial tissues.

13. The apparatus according to claim 10 wherein said tissues comprise sensory retina tissues.

14. The apparatus according to claim 10 wherein said tissues comprise stem cells.

15. The apparatus according to claim 3 wherein said device in communication with said passage is capable of delivering pharmaceutical agents through said passage.

16. The apparatus according to claim 3 wherein said device in communication with said passage is capable of a delivering biologic agent through said passage.

17. The apparatus according to claim 16 wherein said biologic agent comprises a radionuclide.

18. The apparatus according to claim 16 wherein said biologic agent comprises a gene therapy product.

19. The apparatus according to claim 3 wherein said device in communication with said passage is capable of delivering gases through said passage.

20. The apparatus according to claim 3 wherein said device in communication with said passage is capable of aspirating liquids through said passage.

21. The apparatus according to claim 3 wherein said device in communication with said passage is capable of aspirating gases through said passage.

22. The apparatus according to claim 1 or 2 wherein said annular space in said first elongated tubular member is in communication with a device for introducing fluids, suspensions, viscous solids or gases, or aspirating fluids, suspensions, viscous solids or gases, through said passage.

23. The apparatus according to claim 1 or 2 wherein the distal end of said second elongated tubular member is adapted to extend beyond the open distal end of said first elongated tubular member.

24. The apparatus according to claim 23 wherein said second elongated tubular member is adapted to extend beyond the open distal end of said first elongated tubular member by about 0.0015 inch to about 0.125 inch.

25. The apparatus according to claim 1 or 2 wherein said second elongated tubular member is slidably disposed within said first elongated tubular member.

26. The apparatus according to claim 25 wherein said second elongated tubular member is retractable into the lumen of said first elongated tubular member.

27. The apparatus according to claim 1 or 2 wherein said first or second elongated tubular member comprises a metal.

28. The apparatus according to claim 27 wherein said metal comprises stainless steel.

29. The apparatus according to claim 27 wherein said second elongated tubular member comprises a nickel-titanium alloy.

30. The apparatus according to claim 1 or 2 wherein said passage accommodates a surgical instrument or tool.

31. The apparatus according to claim 30 wherein said tool comprises an imaging instrument.

32. The apparatus according to claim 31 wherein said imaging instrument comprises an endoscope.

33. The apparatus according to claim 30 wherein said instrument comprises a microsurgical instrument.

34. The apparatus according to claim 30 wherein said instrument or tool is used for removal of blood clots from tissues or vessels.

35. The apparatus according to claim 30 wherein said instrument comprises a fiber optic instrument.

36. The apparatus according to claim 35 wherein said fiber optic instrument is an imaging instrument.

37. The apparatus according to claim 35 wherein said fiber optic instrument is adapted to deliver energy at a target site.

38. The apparatus according to claim 37 wherein said fiber optic instrument is adapted to deliver laser energy for ablation of tissues or vessels.

39. The apparatus according to claim 37 wherein said fiber optic instrument is adapted to deliver radio frequency energy for ablation of tissues or vessels.

40. The apparatus according to claim 1 or 2 wherein said first elongated tubular member is suitably sized to pass through a sclerostomy port.

41. The apparatus according to claim 1 or 2 wherein the distal end of said second elongated tubular member is shaped and dimensioned for access to the tissue of the retinal pigment epithelium.

42. The apparatus according to claim 1 or 2 wherein the distal end of said second elongated tubular member is shaped and dimensioned for access to the tissue of the sub-retinal space.

* * * * *